US010647829B2

(12) United States Patent
Minagawa

(10) Patent No.: US 10,647,829 B2
(45) Date of Patent: *May 12, 2020

(54) SURFACE MODIFICATION METHOD AND SURFACE MODIFICATION BODY

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/896,096

(22) PCT Filed: May 20, 2014

(86) PCT No.: PCT/JP2014/063268
§ 371 (c)(1),
(2) Date: Dec. 4, 2015

(87) PCT Pub. No.: WO2014/203668
PCT Pub. Date: Dec. 24, 2014

(65) Prior Publication Data
US 2016/0122488 A1  May 5, 2016

(30) Foreign Application Priority Data
Jun. 20, 2013 (JP) ................. 2013-129763

(51) Int. Cl.
C08J 7/18 (2006.01)
A61L 27/50 (2006.01)
A61L 29/14 (2006.01)
C08J 7/12 (2006.01)
C08F 291/02 (2006.01)
A61L 31/10 (2006.01)
B01D 15/38 (2006.01)
B01D 39/16 (2006.01)

(52) U.S. Cl.
CPC ................ C08J 7/18 (2013.01); A61L 27/50 (2013.01); A61L 29/14 (2013.01); A61L 31/10 (2013.01); B01D 15/38 (2013.01); B01D 39/16 (2013.01); C08F 291/02 (2013.01); C08J 7/123 (2013.01); A61L 2400/18 (2013.01); A61L 2420/02 (2013.01); C08J 2325/06 (2013.01); C08J 2327/18 (2013.01); C08J 2367/02 (2013.01)

(58) Field of Classification Search
None
See application file for complete search history.

(56) References Cited

U.S. PATENT DOCUMENTS

| | | |
|---|---|---|
| 3,418,066 A | 12/1968 | Caldwell et al. |
| 5,100,689 A | 3/1992 | Goldberg et al. |
| 5,154,727 A | 10/1992 | Dyer |
| 5,340,879 A | 8/1994 | Audenaert et al. |
| 5,443,511 A | 8/1995 | Ogawa et al. |
| 5,453,467 A | 9/1995 | Bamford et al. |
| 5,637,460 A | 6/1997 | Swan et al. |
| 5,688,252 A | 11/1997 | Matsuda et al. |
| 5,688,747 A | 11/1997 | Khan et al. |
| 5,855,623 A | 1/1999 | English et al. |
| 5,858,545 A | 1/1999 | Everaerts et al. |
| 5,885,566 A | 3/1999 | Goldberg |
| 5,889,073 A | 3/1999 | Zhang et al. |
| 5,954,869 A | 9/1999 | Elfersy et al. |
| 5,967,714 A | 10/1999 | Ottersbach et al. |
| 6,001,894 A | 12/1999 | Ottersbach et al. |
| 6,188,075 B1 | 2/2001 | Takayama et al. |
| 6,203,856 B1 | 3/2001 | Ottersbach et al. |
| 6,228,172 B1 | 5/2001 | Taylor et al. |
| 6,358,557 B1 | 3/2002 | Wang et al. |
| 6,458,867 B1 | 10/2002 | Wang et al. |

(Continued)

FOREIGN PATENT DOCUMENTS

| | | |
|---|---|---|
| CN | 1635915 A | 7/2005 |
| CN | 101372538 A | 2/2009 |

(Continued)

OTHER PUBLICATIONS

English machine translation of WO2012/165525. Sumitomo.*

(Continued)

Primary Examiner — Kara M Peo
(74) Attorney, Agent, or Firm — Birch, Stewart, Kolasch & Birch, LLP

(57) ABSTRACT

Provided are methods for surface-modifying a rubber vulcanizate or a thermoplastic resin, which can provide chemically fixed surfaces showing low adsorption properties or selective adsorption properties with respect to proteins and cells, as well as excellent durability, instead of coatings which have drawbacks, such as that the performance is reduced due to separation or peeling of the coating. The present invention relates to a method for surface-modifying an object made of a rubber vulcanizate or a thermoplastic resin, the method including: a step 1 of forming polymerization initiation points on the surface of the object; and a step 2 of radically polymerizing a hydrophilic monomer starting from the polymerization initiation points by irradiation with UV light having a wavelength of 300 to 400 nm to grow polymer chains on the surface of the object.

6 Claims, No Drawings

(56) References Cited

U.S. PATENT DOCUMENTS

| | | |
|---|---|---|
| 6,599,558 B1 | 7/2003 | Al-Lamee et al. |
| 6,808,738 B2 | 10/2004 | Ditizio et al. |
| 6,986,868 B2 | 1/2006 | Madsen |
| 7,160,592 B2 | 1/2007 | Rypacek et al. |
| 7,348,055 B2 | 3/2008 | Chappa et al. |
| 8,299,139 B1 | 10/2012 | Taranekar et al. |
| 8,323,750 B2 | 12/2012 | Yang et al. |
| 8,840,927 B2 | 9/2014 | Ditizio et al. |
| 9,339,845 B2 | 5/2016 | Minagawa |
| 9,469,736 B2 | 10/2016 | Minagawa |
| 9,758,605 B2 | 9/2017 | Minagawa |
| 9,982,105 B2 | 5/2018 | Minagawa |
| 2002/0002363 A1 | 1/2002 | Urakawa et al. |
| 2002/0161065 A1 | 10/2002 | Ditizio et al. |
| 2003/0139620 A1 | 7/2003 | Yamaguchi et al. |
| 2004/0071909 A1 | 4/2004 | McGlothlin et al. |
| 2004/0086568 A1 | 5/2004 | Ditizio et al. |
| 2004/0106732 A1 | 6/2004 | Tsuji et al. |
| 2005/0137355 A1 | 6/2005 | Buckanin et al. |
| 2005/0168685 A1 | 8/2005 | Katagiri et al. |
| 2006/0155057 A1 | 7/2006 | Hermeling et al. |
| 2006/0207723 A1 | 9/2006 | Kuhn et al. |
| 2007/0003592 A1 | 1/2007 | Hissink |
| 2007/0048349 A1 | 3/2007 | Salamone et al. |
| 2007/0116971 A1 | 5/2007 | Yoshikawa et al. |
| 2007/0197681 A1 | 8/2007 | Lowery et al. |
| 2007/0275171 A1 | 11/2007 | Dang et al. |
| 2008/0016644 A1 | 1/2008 | Mizote et al. |
| 2008/0103287 A1 | 5/2008 | Chino et al. |
| 2008/0281396 A1 | 11/2008 | Ishida et al. |
| 2008/0312377 A1 | 12/2008 | Schmidt et al. |
| 2008/0317991 A1 | 12/2008 | Pieslak et al. |
| 2009/0117303 A1 | 5/2009 | Goshiki |
| 2009/0169715 A1 | 7/2009 | Dias et al. |
| 2009/0239089 A1 | 9/2009 | Agata et al. |
| 2009/0257022 A1 | 10/2009 | Abe et al. |
| 2009/0280157 A1 | 11/2009 | Maas et al. |
| 2009/0317443 A1 | 12/2009 | Willis et al. |
| 2010/0053547 A1 | 3/2010 | Baude et al. |
| 2010/0076546 A1 | 3/2010 | Dias et al. |
| 2010/0247890 A1 | 9/2010 | Habassi et al. |
| 2010/0255336 A1 | 10/2010 | Zabinski |
| 2011/0086234 A1 | 4/2011 | Stasko et al. |
| 2011/0124766 A1* | 5/2011 | Yang .............. C07D 311/86 522/126 |
| 2011/0159101 A1 | 6/2011 | Kurdyumov et al. |
| 2011/0160357 A1 | 6/2011 | Gerster et al. |
| 2011/0263011 A1 | 10/2011 | Qiu et al. |
| 2011/0274940 A1 | 11/2011 | Kyomoto et al. |
| 2011/0313363 A1* | 12/2011 | D'Souza .............. A61M 5/3129 604/187 |
| 2012/0021151 A1 | 1/2012 | Tatarka et al. |
| 2012/0100369 A1 | 4/2012 | Hanazawa et al. |
| 2012/0324751 A1 | 12/2012 | Wakeman |
| 2013/0158488 A1 | 6/2013 | Weaver et al. |
| 2013/0158518 A1 | 6/2013 | Li et al. |
| 2013/0203883 A1 | 8/2013 | Minagawa |
| 2013/0274367 A1 | 10/2013 | Minagawa et al. |
| 2013/0303689 A1 | 11/2013 | Sato et al. |
| 2013/0310772 A1 | 11/2013 | Minagawa |
| 2014/0039084 A1 | 2/2014 | Minagawa |
| 2014/0128493 A1 | 5/2014 | Minagawa |
| 2014/0322468 A1 | 10/2014 | Minagawa |
| 2015/0203612 A1 | 7/2015 | Minagawa |
| 2015/0329755 A1 | 11/2015 | Hakoshima et al. |
| 2016/0122488 A1 | 5/2016 | Minagawa |
| 2016/0213820 A1 | 7/2016 | Minagawa et al. |
| 2016/0281216 A1 | 9/2016 | Shibusawa |

FOREIGN PATENT DOCUMENTS

| | | |
|---|---|---|
| CN | 101565489 A | 10/2009 |
| CN | 202427397 U | 9/2012 |
| CN | 102780256 A | 11/2012 |
| CN | 103193927 A | 7/2013 |
| CN | 103242553 A | 8/2013 |
| CN | 104119552 A | 10/2014 |
| EP | 0810239 A2 | 12/1997 |
| EP | 0 872 512 A2 | 10/1998 |
| EP | 2 623 335 A2 | 8/2013 |
| EP | 2 664 627 A1 | 11/2013 |
| EP | 2 796 155 A1 | 10/2014 |
| EP | 2 894 191 A1 | 7/2015 |
| GB | 1120803 A | 7/1968 |
| GB | 1120804 A | 7/1968 |
| JP | 60-221410 A | 11/1985 |
| JP | 62-87163 A | 4/1987 |
| JP | 63-92658 A | 4/1988 |
| JP | 4-250158 A | 9/1992 |
| JP | 5-43634 A | 2/1993 |
| JP | 5-76590 A | 3/1993 |
| JP | 5-115541 A | 5/1993 |
| JP | 5-179055 A | 7/1993 |
| JP | 6-25450 A | 2/1994 |
| JP | 6-510322 A | 11/1994 |
| JP | 7-47120 A | 2/1995 |
| JP | 7-100744 B2 | 11/1995 |
| JP | 7-289630 A | 11/1995 |
| JP | 8-1793 A | 1/1996 |
| JP | 9-31361 A | 2/1997 |
| JP | 9-67457 A | 3/1997 |
| JP | 9-108359 A | 4/1997 |
| JP | 9-313594 A | 12/1997 |
| JP | 10-231 A | 1/1998 |
| JP | 10-17688 A | 1/1998 |
| JP | 10-90500 A | 4/1998 |
| JP | 10-251350 A | 9/1998 |
| JP | 10-298320 A | 11/1998 |
| JP | 10-330383 A | 12/1998 |
| JP | 11-192305 A | 7/1999 |
| JP | 2001-29452 A | 2/2001 |
| JP | 2001-31871 A | 2/2001 |
| JP | 2001-46956 A | 2/2001 |
| JP | 2001-95621 A | 4/2001 |
| JP | 2001-164176 A | 6/2001 |
| JP | 2002-502286 A | 1/2002 |
| JP | 2002-145971 A | 5/2002 |
| JP | 2003-2903 A | 1/2003 |
| JP | 2003-510378 A | 3/2003 |
| JP | 2003-520107 A | 7/2003 |
| JP | 2004-528418 A | 9/2004 |
| JP | 2004-298220 A | 10/2004 |
| JP | 2005-3817 A | 1/2005 |
| JP | 2005-516736 A | 6/2005 |
| JP | 2005-186577 A | 7/2005 |
| JP | 2005-208290 A | 8/2005 |
| JP | 2005-213516 A | 8/2005 |
| JP | 2005-523981 A | 8/2005 |
| JP | 2005-253538 A | 9/2005 |
| JP | 2006-61273 A | 3/2006 |
| JP | 2007-119563 A | 5/2007 |
| JP | 2007-145884 A | 6/2007 |
| JP | 2007-514861 A | 6/2007 |
| JP | 2007-196211 A | 8/2007 |
| JP | 2007-202965 A | 8/2007 |
| JP | 2008-73883 A | 4/2008 |
| JP | 2009-30074 A | 2/2009 |
| JP | 2009-518479 A | 5/2009 |
| JP | 2009-138169 A | 6/2009 |
| JP | 2009-226718 A | 10/2009 |
| JP | 2010-23710 A | 2/2010 |
| JP | 2010-508541 A | 3/2010 |
| JP | 2010-142537 A | 7/2010 |
| JP | 2010-142573 A | 7/2010 |
| JP | 2010-150349 A | 7/2010 |
| JP | 4523532 B2 | 8/2010 |
| JP | 2010-216964 A | 9/2010 |
| JP | 2010-229180 A | 10/2010 |
| JP | 2011-42755 A | 3/2011 |
| JP | 2011-67362 A | 4/2011 |
| JP | 2011-188908 A | 9/2011 |
| JP | 2011-189562 A | 9/2011 |
| JP | 2011-208133 A | 10/2011 |

(56) References Cited

FOREIGN PATENT DOCUMENTS

| | | |
|---|---|---|
| JP | 2011-219520 A | 11/2011 |
| JP | 2011-241190 A | 12/2011 |
| JP | 2012-6390 A | 1/2012 |
| JP | 2012-105579 A | 6/2012 |
| JP | 2012-162646 A | 8/2012 |
| JP | 2013-159629 A | 8/2013 |
| JP | 2013-159667 A | 8/2013 |
| JP | 2013-208777 A | 10/2013 |
| JP | 2013-237801 A | 11/2013 |
| JP | 2013-237802 A | 11/2013 |
| JP | 2014-31428 A | 2/2014 |
| JP | 2014-31429 A | 2/2014 |
| JP | 2014-31430 A | 2/2014 |
| JP | 2014-108153 A | 6/2014 |
| JP | 2014-214226 A | 11/2014 |
| JP | 2015-502438 A | 1/2015 |
| JP | 2015-107312 A | 6/2015 |
| JP | 6034506 B2 | 11/2016 |
| WO | WO 93/05081 A1 | 3/1993 |
| WO | WO 01/52915 A1 | 7/2001 |
| WO | WO 01/60923 A1 | 8/2001 |
| WO | WO 03/022322 A2 | 3/2003 |
| WO | WO 03/068289 A1 | 8/2003 |
| WO | WO 03/093357 A1 | 11/2003 |
| WO | WO 2007/065721 A2 | 6/2007 |
| WO | WO 2007/072613 A1 | 6/2007 |
| WO | WO 2008/023604 A1 | 2/2008 |
| WO | WO 2008/053712 A1 | 5/2008 |
| WO | WO 2009/009628 A2 | 1/2009 |
| WO | WO 2009/012353 A2 | 1/2009 |
| WO | WO 2009/085817 A1 | 7/2009 |
| WO | WO 2010/058848 A1 | 5/2010 |
| WO | WO 2010/131652 A1 | 11/2010 |
| WO | WO 2011/038483 A1 | 4/2011 |
| WO | WO 2011/047013 A1 | 4/2011 |
| WO | WO 2011/076924 A1 | 6/2011 |
| WO | WO 2012/091169 A1 | 7/2012 |
| WO | WO 2012/096320 A1 | 7/2012 |
| WO | WO 2013/016849 A1 | 2/2013 |
| WO | WO 2014/148479 A1 | 9/2014 |
| WO | WO 2014/203668 A1 | 12/2014 |

OTHER PUBLICATIONS

International Search Report, issued in PCT/JP2014/063268, dated Aug. 19, 2014.
International Search Report and English translation thereof, dated Jan. 21, 2014, for International Application No. PCT/JP2013/081090.
Jinan Haohua Industry Co., Ltd., "Ethanaminum, N,N,N-trimethyl-2-[(2-methyl-1-oxo-2-propen-1-yl) oxy]-, chloride (1:1)," CAS: 5039-78-1, Product Information Inquiry Description, found online on Dec. 27, 2016, pp. 1-2 (3 pages), http://guide7932.guidechem.com/pro-show2436647.html.
U.S. Non-Final Office Action, dated May 8, 2015, for U.S. Appl. No. 13/756,837.
U.S. Non-Final Office Action, dated Oct. 20, 2014, for U.S. Appl. No. 13/756,837.
U.S. Notice of Allowance, dated Dec. 26, 2014, for U.S. Appl. No. 13/956,974.
U.S. Office Action (Requirement for Restriction/Election), dated May 9, 2014, for U.S. Appl. No. 13/956,974.
U.S. Office Action dated Jun. 24, 2015, for U.S. Appl. No. 14/118,136.
U.S. Office Action dated Sep. 21, 2015, for U.S. Appl. No. 14/107,746.
U.S. Office Action, dated Apr. 17, 2015, for U.S. Appl. No. 13/775,451.
U.S. Office Action, dated Aug. 25, 2014, for U.S. Appl. No. 13/956,974.
English translation of Chinese Office Action, dated Sep. 22, 2017, for Chinese Application No. 201380044153.X.
English translation of Chinese Office Action for Appl. No. 201480032195.6 dated Jan. 24, 2018.
Zhang, J., et al, "Corona Radiation Technology" China Textile Press, May 2003, p. 14.
International Search Report (Form PCT/ISA/210) for International Application No. PCT/JP2014/082367, dated Mar. 3, 2015, with an English translation.
Written Opinion of the International Searching Authority (Form PCT/ISA/237) for International Application No. PCT/JP2014/082367, dated Mar. 3, 2015, with an English translation.
International Search Report and English translation for Application No. PCT/JP2015/070547 (PCT/ISA/210) dated Oct. 6, 2015.
Written Opinion of the International Searching Authority and English translation for Application No. PCT/JP2015/070547 (PCT/ISA/237) dated Oct. 6, 2015.
Odian, "Principles of polymerization," John Wiley & Sons, 4th Ed., 2004, p. 261 (3 pages total).
Placzek et al., "Photosensitizing properties of compounds related to benzophenone," Acta Dermato-Venereologica, vol. 93, No. 1, 2013, pp. 30-32.
U.S. Office Action dated Jan. 10, 2019 for U.S. App. No. 15/036,100.
Arkles, "Hydrophobicity, Hydrophilicity and Silane Surface Modification", Gelest, Self-Assembled Monolayers (SAMs), Version 2.0, 2011, pp. 1-80 (84 pages total), XP-55098863.
Chin-Quee, et al., "Endothelial Cell Recovery, Acute Thrombogenicity, and Monocyte Adhesion and Activation on Fluorinated Copolymer and Phosphorylcholine Polymer Stent Coatings," Biomaterials, vol. 31, 2010 (published online Oct. 12, 2009), pp. 648-657.
International Search Report (Form PCT/ISA/210), issued in PCT/JP2014/076887, dated Dec. 22, 2014.
Partial English translation of Chinese Office Action for Chinese Application No. 201480054969.5, dated May 2, 2018.
Stasko et al., "Nitric oxide-releasing sol-gel coatings on titanium implants", SciFinder, Accession No. 2011: 467726, 2011, pp. 2-6 (5 pages).
Written Opinion of the International Searching Authority (Form PCT/ISA/237), issued in PCT/JP2014/076887, dated Dec. 22, 2014, with an English translation.
Xue et al., "Surface Modification and Physical Property Study of Inorganic Nanomaterials," 1st Edition, Hefei Industrial University Press, Oct. 31, 2009, pp. 122-123 (4 pages total).
Author Unknown, "tetra-n-propyl silicate", CAS Registry No. 682-01-9, SciFinder®, 2019, 1 page.
Author Unknown, "Unspecified", CAS Registry No. 308068-81-7, SciFinder®, 2019, p. 2 (1 page).
English maching translation of Japanese Publication No. 2001-164176-A.

* cited by examiner

SURFACE MODIFICATION METHOD AND SURFACE MODIFICATION BODY

TECHNICAL FIELD

The present invention relates to methods for surface modification which provide surfaces with low adhesion properties with respect to proteins and cells in blood or biological fluids or selective adhesion properties with respect to cancer cells or the like. The present invention also relates to surface-modified bodies of, for example, matrices, filters, channels, and tubes for medical and healthcare use, having surfaces at least partially modified by the methods.

BACKGROUND ART

Matrices, filters, channels, tubes, and other devices for medical and healthcare use or other uses have a drawback in that since they come into contact with blood or biological fluids inside or outside the body during use, proteins and cells in the blood or biological fluids adhere or adsorb to the surface of the devices and thereby impair the original function of the devices. Meanwhile, there is a need for specific cells such as cancer cells to be selectively adsorbed and collected for capture and use in diagnosis or treatment. However, unfortunately, it is difficult to selectively adsorb these specific cells.

Patent Literatures 1 and 2 propose to coat the surface of matrices, filters, channels, or tubes for medical and healthcare use with a polymer of a hydrophilic monomer to solve the problems mentioned above. However, these methods have a durability problem in that the coating layer is separated or peeled due to the hydrophilicity.

CITATION LIST

Patent Literature

Patent Literature 1: JP 2005-516736 T
Patent Literature 2: JP 2005-523981 T

SUMMARY OF INVENTION

Technical Problem

The present invention aims to solve the aforementioned problems and provide methods for surface-modifying a rubber vulcanizate or a thermoplastic resin, which can provide chemically fixed surfaces showing low adsorption properties or selective adsorption properties with respect to proteins and cells, as well as excellent durability, instead of coatings which have drawbacks, such as that the performance is reduced due to separation or peeling of the coating. The present invention also aims to provide surface-modified bodies of, for example, matrices, filters, channels, and tubes for medical and healthcare use, having surfaces at least partially modified by the methods.

Solution to Problem

The present invention relates to a method for surface-modifying an object made of a rubber vulcanizate or a thermoplastic resin, the method including:
a step 1 of forming polymerization initiation points on a surface of the object; and
a step 2 of radically polymerizing a hydrophilic monomer starting from the polymerization initiation points by irradiation with UV light having a wavelength of 300 to 400 nm to grow polymer chains on the surface of the object.

The present invention relates to a method for surface-modifying an object made of a rubber vulcanizate or a thermoplastic resin, the method including
a step I of radically polymerizing a hydrophilic monomer in the presence of a photopolymerization initiator by irradiation with UV light having a wavelength of 300 to 400 nm to grow polymer chains on a surface of the object.

The step 1 preferably includes adsorbing a photopolymerization initiator to the surface of the object, and then optionally irradiating the surface with UV light having a wavelength of 300 to 400 nm, to form the polymerization initiation points from the photopolymerization initiator on the surface.

The photopolymerization initiator is preferably at least one of a benzophenone compound or a thioxanthone compound.

The surface of the object is preferably irradiated with UV light having a wavelength of 300 nm or less prior to the step 1 or step I.

It is preferred that during or before the light irradiation, an inert gas is inserted into a reaction vessel, a reaction tube, and a reaction solution, and the monomer is polymerized in an atmosphere replaced with the inert gas.

The radical polymerization of the hydrophilic monomer in the step 2 or step I is preferably carried out by applying or spraying a solution of the hydrophilic monomer onto the surface of the object, and then covering the applied or sprayed object with a transparent cover of glass or resin, followed by irradiation with the UV light through the transparent cover of glass or resin to radically polymerize the monomer.

It is preferred that after the step 2 or step I, the surface-modified body on which polymer chains are grown is washed.

The washing is preferably carried out by at least one selected from the group consisting of hot water washing, alcohol washing, and acetone washing.

The hydrophilic monomer is preferably at least one selected from the group consisting of acrylic acid, acrylic acid esters, alkali metal salts of acrylic acid, amine salts of acrylic acid, methacrylic acid, methacrylic acid esters, alkali metal salts of methacrylic acid, amine salts of methacrylic acid, acrylonitrile, acrylamide, dimethylacrylamide, diethylacrylamide, isopropylacrylamide, hydroxyethylacrylamide, methoxyethylacrylamide, acryloylmorpholine, methacrylamide, dimethylmethacrylamide, diethylmethacrylamide, isopropylmethacrylamide, hydroxyethylmethacrylamide, methoxyethylmethacrylamide, and methacryloylmorpholine.

The hydrophilic monomer is preferably an alkali metal-containing monomer.

The alkali metal-containing monomer is preferably at least one selected from alkali metal salts of acrylic acid, methacrylic acid, itaconic acid, 3-vinylpropionic acid, vinylsulfonic acid, 2-sulfoethyl (meth)acrylate, 3-sulfopropyl (meth)acrylate, 2-acrylamide-2-methylpropanesulfonic acid, or styrenesulfonic acid.

The hydrophilic monomer is preferably at least one selected from the group consisting of a zwitterionic monomer and the alkali metal-containing monomer.

Preferably, the solution of the hydrophilic monomer contains a polymerization inhibitor, and the monomer is polymerized in the presence of the polymerization inhibitor. The polymerization inhibitor is preferably 4-methylphenol. The polymer chains preferably each have a length of 10 to 50000 nm.

The present invention relates to a surface-modified body, produced by any of the methods.

The present invention relates to a surface-modified body, produced by any of the methods, to which proteins and cells in blood or biological fluids are less likely to adhere or adsorb.

The present invention relates to a surface-modified body, produced by any of the methods, to which a specific protein or specific cells in blood or biological fluids is more likely to selectively adhere or adsorb.

The present invention relates to a surface-modified body, including a three-dimensional solid having a surface at least partially modified by any of the methods.

The surface-modified body preferably includes a polymer brush.

The present invention relates to a matrix for medical and healthcare use, having a surface at least partially modified by any of the methods.

The present invention relates to a filter for medical and healthcare use, having a surface at least partially modified by any of the methods.

The filter preferably has a porous structure or pillar structure.

The present invention relates to a channel for medical and healthcare use, having a surface at least partially modified by any of the methods.

The present invention relates to a tube for medical and healthcare use, having a surface at least partially modified by any of the methods.

Advantageous Effects of Invention

The methods for surface-modifying an object made of a rubber vulcanizate or a thermoplastic resin of the present invention include a step 1 of forming polymerization initiation points on the surface of the object, and a step 2 of radically polymerizing a hydrophilic monomer starting from the polymerization initiation points by irradiation with UV light having a wavelength of 300 to 400 nm to grow polymer chains on the surface of the object, or include a step I of radically polymerizing a hydrophilic monomer in the presence of a photopolymerization initiator by irradiation with UV light having a wavelength of 300 to 400 nm to grow polymer chains on the surface of the object. Such methods enable the objects to have a surface with a hydrophilic polymer fixed thereon and, therefore, to get not only low adsorption properties with respect to proteins and cells or selective adsorption properties with respect to a specific protein or specific cells, but also durability after repeated use, thereby sufficiently suppressing deterioration of the low adhesion properties or selective adhesion properties. Thus, by forming hydrophilic polymer chains on the surface of an object using such a method, it is possible to produce surface-modified bodies of, for example, matrices, filters, channels, and tubes for medical and healthcare use, which are excellent in these properties.

DESCRIPTION OF EMBODIMENTS

One aspect of the present invention is a method for surface-modifying an object made of a rubber vulcanizate or a thermoplastic resin, the method including: a step 1 of forming polymerization initiation points on the surface of the object; and a step 2 of radically polymerizing a hydrophilic monomer starting from the polymerization initiation points by irradiation with UV light having a wavelength of 300 to 400 nm to grow polymer chains on the surface of the object.

In the step 1, polymerization initiation points are formed on the surface of a molded rubber vulcanizate or a molded thermoplastic resin (an object to be modified). For example, the step 1 may be carried out by adsorbing a photopolymerization initiator to the surface of the object to form the polymerization initiation points, or by adsorbing a photopolymerization initiator to the surface of the object and then irradiating the surface with UV light having a wavelength of 300 to 400 nm to form the polymerization initiation points from the photopolymerization initiator on the surface.

Examples of thermoplastic resins that can be used as the object to be modified include polyester resin such as polyethylene terephthalate (PET), polyimide resin, polystyrene, polypropylene, cyclic polyolefin, polycarbonate, polytetrafluoroethylene, polydimethylsiloxane, acrylic resin, methacrylic resin, and methyl methacrylic resin.

Examples of rubbers that can be used as the object to be modified include silicone rubber, fluororubber, natural rubber, deproteinized natural rubber, styrene-butadiene rubber, polybutadiene rubber, polyisoprene rubber, and butyl rubber and halogenated butyl rubber which have a degree of unsaturation of a few percent of isoprene units.

The conditions for vulcanization of the rubber may be appropriately set, and the vulcanization temperature of the rubber is preferably 140° C. or higher, more preferably 170° C. or higher, and still more preferably 175° C. or higher.

Examples of the photopolymerization initiator include carbonyl compounds, organic sulfur compounds such as tetraethylthiuram disulfide, persulfides, redox compounds, azo compounds, diazo compounds, halogen compounds, and photoreducing dyes. Preferred among these are carbonyl compounds.

Preferred among carbonyl compounds serving as photopolymerization initiators are benzophenone and derivatives thereof (benzophenone compounds). For example, suitable are benzophenone compounds represented by the following formula:

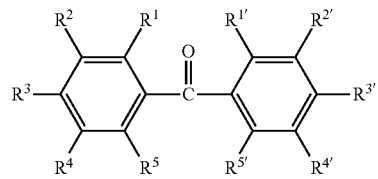

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxyl group, a primary to tertiary amino group, a mercapto group, or a hydrocarbon group optionally containing an oxygen, nitrogen, or sulfur atom, and any two adjacent groups of $R^1$ to $R^5$ and to $R^{5'}$ may be joined together to form a cyclic structure with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Particularly preferred among these are benzophenone, xanthone, and 9-fluorenone because these compounds allow polymer brushes to be formed well.

The photopolymerization initiator may also suitably be a thioxanthone compound because it provides a high polymerization rate and can easily be adsorbed on and/or reacted with rubber or the like. For example, suitable are compounds represented by the following formula:

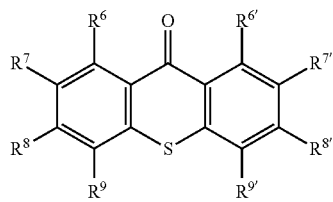

wherein $R^6$ to $R^9$ and $R^{6'}$ to $R^{9'}$ are the same as or different from one another and each represent a hydrogen atom, a halogen atom, or an alkyl, cyclic alkyl, aryl, alkenyl, alkoxy, or aryloxy group.

Examples of thioxanthone compounds represented by the above formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, 2-methoxythioxanthone, and 2-p-octyloxyphenyl-4-ethylthioxanthone. Preferred among these are those which are substituted at one or two, especially two, of $R^6$ to $R^9$ and $R^{6'}$ to $R^{9'}$ with alkyl groups. More preferred is 2,4-diethylthioxanthone.

The adsorption of a photopolymerization initiator such as a benzophenone or thioxanthone compound on the surface of the object to be modified may be carried out as follows. In the case of using a benzophenone or thioxanthone compound, for example, the benzophenone or thioxanthone compound is dissolved in an organic solvent to prepare a solution; a surface portion of the object to be modified is treated with this solution so that the compound is adsorbed on the surface; and, if necessary, the organic solvent is dried and evaporated, whereby polymerization initiation points are formed. The surface-treating method may be any method that allows the solution of the benzophenone or thioxanthone compound to be brought into contact with the surface of the object. Suitable methods include, for example, application or spraying of the benzophenone or thioxanthone compound solution, and immersion into the solution. Moreover, if only part of the surface needs to be modified, it is sufficient to adsorb the photopolymerization initiator only to the necessary part of the surface. In this case, for example, application or spraying of the solution is suitable. Examples of the solvent include methanol, ethanol, acetone, benzene, toluene, methyl ethyl ketone, ethyl acetate, and THF. Acetone is preferred because it does not swell the object and it is quickly dried or evaporated.

As described, after the photopolymerization initiator is adsorbed on the surface of the object, the surface may then be irradiated with UV light having a wavelength of 300 to 400 nm to form the polymerization initiation points from the photopolymerization initiator on the surface. This irradiation with UV light can be carried out by known methods. For example, it may be carried out by the method used in the irradiation with UV light in the step 2 which will be described later.

In the step 2, a hydrophilic monomer is radically polymerized starting from the polymerization initiation points formed in the step 1, by irradiation with UV light having a wavelength of 300 to 400 nm to grow polymer chains on the surface of the object.

The hydrophilic monomer may be a monomer containing a functional group that can be converted to a hydrophilic functional group, and examples include monomers containing hydrophilic groups, such as an amide group, a sulfuric acid group, a sulfonic acid group, a carboxylic acid group, a hydroxyl group, an amino group, an amide group, an oxyethylene group, or precursor functional groups of these groups.

Specific examples of the hydrophilic monomer include (meth)acrylic acid, (meth)acrylic acid esters (alkoxyalkyl (meth)acrylates such as methoxyethyl (meth)acrylate and hydroxyalkyl (meth)acrylates such as hydroxyethyl (meth)acrylate), alkali metal salts of (meth)acrylic acid, amine salts of (meth)acrylic acid, and monomers containing a C—N bond in the molecule. Examples of the monomers containing a C—N bond in the molecule include (meth)acrylamide; N-alkyl substituted (meth)acrylamide derivatives (N-ethyl (meth)acrylamide, N-n-propyl(meth)acrylamide, N-isopropyl(meth)acrylamide, N-cyclopropyl(meth)acrylamide, and alkoxyalkyl(meth)acrylamides such as N-methoxymethyl (meth)acrylamide, N-methoxyethyl(meth)acrylamide, and N-ethoxyethyl(meth)acrylamide); N,N-dialkyl substituted (meth)acrylamide derivatives (e.g. N,N-dimethyl(meth) acrylamide, N,N-ethylmethyl(meth)acrylamide, N,N-diethyl(meth)acrylamide); hydroxy(meth)acrylamide; hydroxy(meth)acrylamide derivatives (hydroxyalkyl(meth) acrylamides such as N-hydroxyethyl(meth)acrylamide); and cyclic group-containing (meth)acrylamide derivatives (e.g. (meth)acryloylmorpholine). Preferred among these are (meth)acrylic acid, (meth)acrylic acid esters, alkali metal salts of (meth)acrylic acid, amine salts of (meth)acrylic acid, acrylonitrile, (meth)acrylamide, dimethyl(meth)acrylamide, diethyl(meth)acrylamide, isopropyl(meth)acrylamide, hydroxyethyl(meth)acrylamide, methoxyethyl(meth)acrylamide, methoxymethyl(meth)acrylamide, and (meth)acryloylmorpholine. More preferred are (meth)acryloylmorpholine, methoxymethyl(meth)acrylamide, (meth)acrylamide, and 2-methoxyethyl acrylate, with methoxymethyl(meth) acrylamide or 2-methoxyethyl acrylate being particularly preferred.

The hydrophilic monomer may also suitably be an alkali metal-containing monomer, which is a monomer containing an alkali metal in the molecule, a zwitterionic monomer, which is a zwitterionic group-containing compound (compound bearing a center of permanent positive charge and a center of negative charge), or the like. These may be used alone, or two or more of these may be used in combination.

Examples of the alkali metal-containing monomer include alkali metal salts of acrylic acid, such as sodium acrylate and potassium acrylate; alkali metal salts of methacrylic acid, such as sodium methacrylate and potassium methacrylate; alkali metal salts of itaconic acid, such as sodium itaconate and potassium itaconate; alkali metal salts of 3-vinylpropionic acid, such as sodium 3-vinylpropionate and potassium 3-vinylpropionate; alkali metal salts of vinylsulfonic acid, such as sodium vinylsulfonate and potassium vinylsulfonate; alkali metal salts of 2-sulfoethyl (meth)acrylate, such as sodium 2-sulfoethyl (meth)acrylate and potassium 2-sulfoethyl (meth)acrylate; alkali metal salts of 3-sulfopropyl (meth)acrylate, such as sodium 3-sulfopropyl (meth)acrylate and potassium 3-sulfopropyl (meth)acrylate; alkali metal salts of 2-acrylamide-2-methylpropanesulfonic acid, such as sodium 2-acrylamide-2-methylpropanesulfonate and potassium 2-acrylamide-2-methylpropanesulfonate; and alkali metal salts of styrenesulfonic acid, such as sodium styrenesulfonate and potassium styrenesulfonate.

Examples of the zwitterionic monomer include carboxybetaines, sulfobetaines, phosphobetaines. Other examples include compounds represented by the formula (1) below. Suitable among these compounds are compounds represented by the formula (2) below.

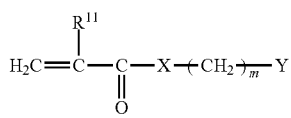
(1)

In the formula, $R^{11}$ represents —H or —CH$_3$; X represents —O—, NH$^-$ or N$^+$—; m represents an integer of 1 or greater; and Y represents a zwitterionic group or a halogen group such as Cl$^-$, Br$^-$, or F$^{31}$.

In the formula (1), it is preferred that $R^{11}$ is —CH$_3$, X is —O—, and m is an integer of 1 to 10. In the zwitterionic group designated by Y, the cation may be a quaternary ammonium such as tetraalkylammonium, and the anion may be a carboxylic acid, sulfonic acid, phosphate or the like.

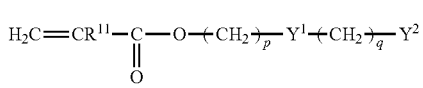
(2)

In the formula, $R^{11}$ represents —H or —CH$_3$; p and q each represent an integer of 1 or greater; and $Y^1$ and $Y^2$ represent ionic functional groups having charges opposite to each other.

In the formula (2), p is preferably an integer of 2 or greater, more preferably an integer of 2 to 10; q is preferably an integer of 1 to 10, more preferably an integer of 2 to 4. Preferred $R^{11}$ groups are as identified above. $Y^1$ and $Y^2$ are as defined for the cation and anion above.

Typical suitable examples of the zwitterionic monomer include compounds represented by the following formulas (2-1) to (2-4):

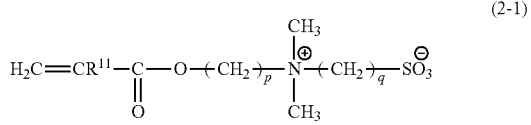
(2-1)

wherein $R^{11}$ represents a hydrogen atom or a methyl group, and p and q each represent an integer of 1 to 10;

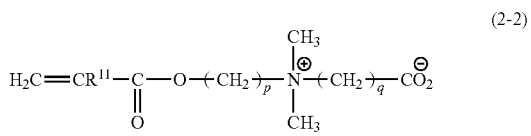
(2-2)

wherein $R^{11}$ represents a hydrogen atom or a methyl group, and p and q each represent an integer of 1 to 10;

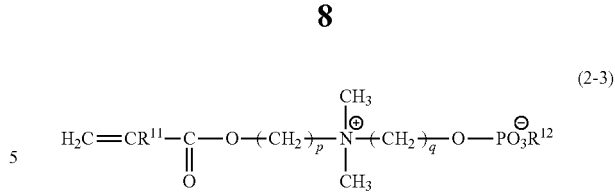
(2-3)

wherein $R^{11}$ represents a hydrogen atom or a methyl group, $R^{12}$ represents a C1-C6 hydrocarbon group, and p and q each represent an integer of 1 to 10; and

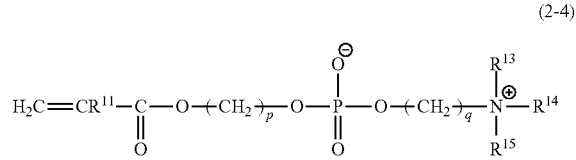
(2-4)

wherein $R^{11}$ represents a hydrogen atom or a methyl group, $R^{13}$, $R^{14}$, and $R^{15}$ are the same as or different from one another and each represent a C1-C2 hydrocarbon group, and p and q each represent an integer of 1 to 10.

Examples of the compound represented by the formula (2-1) include dimethyl(3-sulfopropyl)(2-(meth)acryloyloxyethyl)ammonium betaine. Examples of the compound represented by the formula (2-2) include dimethyl(2-carboxyethyl)-(2-(meth)acryloyloxyethyl)ammonium betaine. Examples of the compound represented by the formula (2-3) include dimethyl(3-methoxyphosphopropyl)-(2-(meth)acryloyloxyethyl)ammonium betaine. Examples of the compound represented by the formula (2-4) include 2-(meth)acryloyloxyethyl phosphorylcholine. The zwitterionic monomer may also be 2-(meth)acryloyloxyethyl carboxybetaine, 2-(meth)acryloyloxyethyl sulfobetaine or the like. Among these, 2-(meth)acryloyloxyethyl phosphorylcholine is preferred because it has high biocompatibility, that is, low protein adsorption properties.

The radical polymerization of a hydrophilic monomer in the step 2 may be carried out as follows: A solution of a hydrophilic monomer is applied (sprayed) onto the surface of the object on which a benzophenone or thioxanthone compound or the like has been adsorbed, or alternatively, the object is immersed in a solution of a hydrophilic monomer; and the object is then irradiated with UV light to allow radical polymerization (photo-radical polymerization) of the monomer to proceed, whereby polymer chains are grown on the surface of the object. After the application, the surface may also be covered with a transparent cover of glass, PET, polycarbonate or the like, and irradiated with light such as ultraviolet light through the cover to allow radical polymerization (photo-radical polymerization) of the monomer to proceed, whereby polymer chains are grown on the surface of the object.

The solvent for application (spraying), the method for application (spraying), the method for immersion, the conditions for irradiation, and the like may be conventionally known materials or methods. The solution of the radically polymerizable monomer may be an aqueous solution, or a solution in an organic solvent that does not dissolve the photopolymerization initiator used (e.g., a benzophenone or thioxanthone compound). Moreover, the solution of the radically polymerizable monomer may contain a known polymerization inhibitor such as 4-methylphenol.

In the present invention, radical polymerization of the hydrophilic monomer is allowed to proceed by light irradiation after the solution of the hydrophilic monomer is applied to the surface, or after the surface is immersed in the hydrophilic monomer or the solution thereof. Here, UV light sources with an emission wavelength mainly in the ultraviolet region, such as high-pressure mercury lamps, metal halide lamps, and LED lamps, can be suitably used. The light dose may be appropriately chosen in view of polymerization time and uniformity of the reaction progress. Moreover, in order to prevent inhibition of polymerization due to active gas such as oxygen in the reaction vessel and the reaction tube, oxygen is preferably removed from the reaction vessel, the reaction tube, and the reaction solution during or before the light irradiation. To this end, appropriate operations may be performed. For example, an inert gas such as nitrogen gas or argon gas is inserted into the reaction vessel, the reaction tube, and the reaction solution to discharge active gas such as oxygen from the reaction system and replace the atmosphere in the reaction system with the inert gas. Furthermore, in order to prevent inhibition of the reaction due to oxygen and the like, for example, a measure may appropriately be taken in which an UV light source is placed such that an air layer (oxygen content: 15% or higher) does not exist between the reaction vessel made of glass, plastics or the like and the reaction solution or the object to be modified.

The ultraviolet light has a wavelength of 300 to 400 nm. Such ultraviolet light enables polymer chains to be formed well on the surface of the object. Examples of light sources that can be used include high-pressure mercury lamps, LEDs with a center wavelength of 365 nm, and LEDs with a center wavelength of 375 nm. More preferred is irradiation with LED light having a wavelength of 355 to 380 nm. In particular, LEDs or the like having a center wavelength of 365 nm, which is close to the excitation wavelength (366 nm) of benzophenone, are preferred in view of efficiency. Light with a wavelength of less than 300 nm may break and damage the molecules of the object. Thus, light having a wavelength of 300 nm or more is preferred, and light having a wavelength of 355 nm or more is more preferred because it produces very little damage to the object. Light having a wavelength of more than 400 nm, however, is less likely to activate the photopolymerization initiator, with the result that the polymerization reaction is not allowed to easily proceed. Thus, light having a wavelength of 400 nm or less is preferred. Although LED light is suitable in that it is in a narrow wavelength range and does not contain light with other wavelengths than the center wavelength, mercury lamps and the like can also achieve similar effects to LED light if a filter is used to block light having a wavelength of less than 300 nm.

Another aspect of the present invention is a method for surface-modifying an object made of a rubber vulcanizate or a thermoplastic resin, the method including a step I of radically polymerizing a hydrophilic monomer in the presence of a photopolymerization initiator by irradiation with UV light having a wavelength of 300 to 400 nm to grow polymer chains on the surface of the object. Specifically, a hydrophilic monomer is radically polymerized using a photopolymerization initiator by irradiation with UV light to form polymer chains, whereby a surface-modified body can be produced in which a polymer layer is formed on the surface of the object. The object to be modified, the photopolymerization initiator, and the hydrophilic monomer used in the step I may be as described hereinabove.

For example, the step I may be carried out by contacting the surface of the object with a photopolymerization initiator and a hydrophilic monomer, and then irradiating the surface with LED light having a wavelength of 300 to 400 nm to form polymerization initiation points from the photopolymerization initiator while radically polymerizing the hydrophilic monomer starting from the polymerization initiation points to grow polymer chains.

The radical polymerization of a hydrophilic monomer in the step I may be carried out as follows: A solution of a hydrophilic monomer with a photopolymerization initiator such as a benzophenone or thioxanthone compound is applied (sprayed) onto the surface of the object, or alternatively, the object is immersed in a solution of a hydrophilic monomer with a photopolymerization initiator; and the object is then irradiated with light such as ultraviolet light to allow radical polymerization (photo-radical polymerization) of the monomer to proceed, whereby polymer chains are grown on the surface of the object. Additionally, for example, the surface may also be covered with a transparent cover of glass, PET, polycarbonate or the like, and irradiated with light such as ultraviolet light through the cover as described above. Here, the solvent for application (spraying), the method for application (spraying), the method for immersion, the conditions for irradiation, and the like may be materials or methods as described hereinabove.

In the present invention, before the step 1 or step I, the surface of the object to be modified is preferably irradiated with UV light having a wavelength of 300 nm or less. This generates a hydroxyl group, carboxyl group, or the like on the surface of the object. The resulting surface has higher affinity for the polymerization initiator and can allow the polymerization initiator to be easily adsorbed. As a result, a surface-modified body that exhibits lower protein adsorption and lower cell adsorption and also has higher durability after repeated use can be obtained. The wavelength is more preferably 150 to 280 nm, still more preferably 175 to 270 nm.

The light source for the irradiation with UV light before the step 1 or step I may suitably be a low-pressure mercury lamp or the like which can emit UV light having large peak intensities at 185 nm and 254 nm to efficiently generate a hydroxyl group, carboxyl group, or the like. The light dose and irradiation time may be appropriately chosen in view of uniformity of the reaction progress.

In the present invention, after the step 2 or step I, the surface-modified body on which polymer chains are grown is preferably subjected to washing treatment. This reduces the amount of polymerization initiator left on the surface of the surface-modified body, resulting in lower protein adsorption and lower cell adsorption.

The washing treatment may be carried out by conventional methods, such as immersion and washing in water. Hot water washing, alcohol washing, and acetone washing are preferred. For example, the washing treatment may suitably be carried out under pressure or heating, for example, using an autoclave.

The conditions for the washing treatment are as follows: The pressure is preferably 0.1 to 0.5 MPa, more preferably 0.15 to 0.4 MPa; the temperature is preferably 50° C. to 150° C., more preferably 100° C. to 140° C., still more preferably 110° C. to 140° C.; and the time is preferably 20 to 1000 minutes, more preferably 30 to 500 minutes. The washing treatment carried out under such conditions reduces the amount of polymerization initiator left on the surface of the surface-modified body, resulting in lower protein adsorption and lower cell adsorption.

The polymer chains formed in the step 2 or step I preferably each have a length of 10 to 50000 nm, more preferably 100 to 50000 nm. If the length is less than 10 nm, good low adsorption properties or selective adsorption properties with respect to proteins and cells tend not to be obtained. If the length is more than 50000 nm, a further improvement in low adsorption properties or selective adsorption properties with respect to proteins and cells cannot be expected, while the cost of raw materials tends to be increased because the monomer used is expensive. In addition, in such cases, surface patterns generated by the surface treatment tend to be visible to the naked eye and thereby spoil the appearance and decrease sealing properties.

In the step 2 or step I, two or more kinds of monomers may be radically polymerized simultaneously. Moreover, multiple kinds of polymer chains may be grown on the surface of the object. In the surface modification methods of the present invention, the polymer chains may be cross-linked to one another. In this case, the polymer chains may be cross-linked to one another by ionic crosslinking, cross-linking by a hydrophilic group containing an oxygen atom, or crosslinking by a halogen group such as iodine.

The surface modification methods can be applied to rubber vulcanizates or thermoplastic resins to produce surface-modified bodies. Moreover, the methods may be applied to at least a part of a three-dimensional solid to obtain a surface-modified body with modified properties. Furthermore, preferred examples of such surface-modified bodies include polymer brushes. The term "polymer brush" means an assembly of graft polymer molecules obtained in the "grafting from" approach by surface-initiated polymerization. Moreover, the graft chains are preferably oriented in a direction substantially vertical to the surface of the object because, in such a case, the entropy is reduced and thus the molecular mobility of the graft chains is reduced, which provides lubricity. Furthermore, semidilute or concentrated brushes having a brush density of 0.01 chains/nm$^2$ or higher are preferred.

The surface modification methods may also be applied to rubber vulcanizates or thermoplastic resins to produce medical devices such as matrices, filters, channels, or tubes for medical and healthcare use, at least part of whose surface is modified. The modification may preferably be applied to at least a surface portion to be in contact with blood or biological fluids of a medical device such as a matrix (e.g. a matrix for collecting and adsorbing a specific protein or specific cells, such as cancer cells, from a blood sample or a biological fluid sample), a filter (which preferably has a porous structure with a large number of fine pores or a pillar structure with a large number of pillars placed at appropriate intervals), a channel, or a tube for medical and healthcare use. The modification may be applied to the entire surface. By appropriately selecting the kind of hydrophilic monomer according to the desired properties, proteins and cells in blood or biological fluids can be prevented from adhering or adsorbing to the surface, or selective adhesion or adsorption of cancer cells or the like can be achieved, and it is also possible to obtain excellent durability because the polymer chains are fixed.

EXAMPLES

The following will describe the present invention in more detail with reference to, though not limited to, examples.

Example 1

A 3 wt % solution of benzophenone in acetone was applied to the surface of a polyethylene terephthalate (PET) object intended to be modified, so that benzophenone was adsorbed on the surface, followed by drying. Then, the surface was irradiated with LED light (5 mW/cm$^2$) with a wavelength of 365 nm for 60 minutes while the object was rotated such that the entire surface was irradiated with light.

Subsequently, the surface was immersed in an aqueous solution of acrylamide (1.25 M) in a glass reaction vessel. The reaction vessel was sealed with a rubber stopper, and argon gas was inserted and allowed to bubble through the solution for 120 minutes to remove oxygen. While being rotated, the glass reaction vessel was irradiated with LED light with a wavelength of 365 nm for 300 minutes to cause radical polymerization, whereby polymer chains were grown on the PET surface. Thus, a surface-modified body (polymer brush) was prepared.

Example 2

A 3 wt % solution of benzophenone in acetone was applied to the surface of a PET object intended to be modified, so that benzophenone was adsorbed on the surface, followed by drying.

Subsequently, the surface was immersed in an aqueous solution of acrylamide (1.25 M) in a glass reaction vessel. The reaction vessel was sealed with a rubber stopper, and argon gas was inserted and allowed to bubble through the solution for 120 minutes to remove oxygen. While being rotated, the glass reaction vessel was irradiated with LED light (5 mW/cm$^2$) with a wavelength of 365 nm for 300 minutes to cause radical polymerization, whereby polymer chains were grown on the PET surface. Thus, a surface-modified body (polymer brush) was prepared.

Example 3

An aqueous solution of acrylamide (1.25 M) was prepared using a 0.015 wt % aqueous solution of benzophenone. The surface of a PET object to be modified was immersed in the aqueous solution in a glass reaction vessel. The reaction vessel was sealed with a rubber stopper, and argon gas was inserted and allowed to bubble through the solution for 120 minutes to remove oxygen. While being rotated, the glass reaction vessel was irradiated with LED light (5 mW/cm$^2$) with a wavelength of 365 nm for 300 minutes to cause radical polymerization, whereby polymer chains were grown on the PET surface. Thus, a surface-modified body (polymer brush) was prepared.

Example 4

A surface-modified body (polymer brush) was prepared as in Example 1, except that 2-methacryloyloxyethyl phosphorylcholine was used instead of acrylamide.

Example 5

A surface-modified body (polymer brush in which polymer chains were grown on the polystyrene surface) was prepared as in Example 1, except that polystyrene was used instead of PET.

Example 6

A surface-modified body (polymer brush in which polymer chains were grown on the polytetrafluoroethylene surface) was prepared as in Example 1, except that polytetrafluoroethylene was used instead of PET.

Example 7

A surface-modified body (polymer brush) was prepared as in Example 1, except that 2-methoxyethyl acrylate was used instead of acrylamide.

Example 8

A 3 wt % solution of benzophenone in acetone was applied to the surface of a PET object intended to be modified, so that benzophenone was adsorbed on the surface, followed by drying.

Subsequently, an aqueous solution of acrylamide (1.25 M) was applied to the surface and then the surface was covered with glass. Then, the surface was irradiated with LED light (5 mW/cm$^2$) with a wavelength of 365 nm through the glass for 300 minutes to cause radical polymerization, whereby polymer chains were grown on the PET surface. Thus, a surface-modified body (polymer brush) was prepared.

Example 9

A surface-modified body (polymer brush) was prepared as in Example 7, except that the PET surface to be modified was irradiated using a low-pressure mercury lamp (intensity at 254 nm: 7.2 mW/cm$^2$) for 5 minutes before use.

Example 10

The surface of the surface-modified body obtained in Example 9 was washed with ethanol and then immersed in a volume of water equal to 10 times the volume of the surface-modified body, followed by treatment in an autoclave at 135° C. and 0.32 MPa for 1 hour. Thus, a surface-modified body (polymer brush) was prepared.

Comparative Example 1

In Comparative Example 1, PET which had not been subjected to surface modification was used.

The surface-modified bodies prepared in the examples and the comparative example were evaluated as follows.
(Length of Polymer Chain)

To determine the length of the polymer chain formed on the surface of the surface-modified body, a cross section of the surface-modified body having polymer chains formed thereon was measured with an SEM at an accelerating voltage of 15 kV and a magnification of 1000 times. The thickness of the polymer layer photographed was determined and taken as the length of the polymer chain.
(Protein Adsorption Amount)

The surface of the sample (surface-modified body) was brought into contact with a 1 mg/ml solution of bovine serum albumin (BSA), followed by standing at 37° C. for 3 hours. The surface of the sample was lightly washed with phosphate buffered saline to prepare a protein adsorbed sample. The whole amount of the protein adsorbed sample was put into a 50-ml centrifuge tube, and the proteins adsorbed on the surface of the sample were extracted in accordance with the method described in Section 3.6, Water-soluble proteins, in JIS T9010: 1999, "Test methods relevant to biological safety of rubber products." To the extracted proteins was accurately added 0.5 ml of a 0.1 mol/l aqueous solution of sodium hydroxide, and the proteins were dissolved to prepare a sample solution. Separately, the same procedure was followed without the addition of the sample to prepare a procedural blank.

A volume of 0.2 ml each of the sample solution and reference solutions (BSA solutions (5 to 100 μg/ml)) was accurately weighed and assayed for protein amount by the Lowry method. A calibration curve was prepared using the BSA concentration (μg/ml) and the absorbance of each reference solution, and the protein concentration (μg/ml) per milliliter of the sample solution was calculated from the calibration curve and converted to a value per area of the surface-modified body.
(Protein Adsorption Amount after Durability Testing)

After a protein adsorption test was performed, the surface was immersed and washed in hot water at 70° C. to wash away proteins. The adsorption and washing operations were repeated 10 times, and then a protein adsorption test was performed again to determine the protein adsorption amount after durability testing and the rate of increase from the initial protein adsorption amount.

TABLE 1

|  | Example 1 | Example 2 | Example 3 | Example 4 | Example 5 | Example 6 |
|---|---|---|---|---|---|---|
| Length of polymer chain (nm) | 3000 | 2500 | 2000 | 1500 | 2700 | 800 |
| Protein adsorption amount (μg/cm$^2$) | 0.32 | 0.31 | 0.35 | 0.13 | 0.34 | 0.22 |
| Protein adsorption amount after durability testing (μg/cm$^2$) | 0.33 | 0.32 | 0.37 | 0.14 | 0.35 | 0.23 |
| Rate of increase | 3% | 3% | 6% | 8% | 3% | 5% |

|  | Example 7 | Example 8 | Example 9 | Example 10 | Comparative Example 1 |
|---|---|---|---|---|---|
| Length of polymer chain (nm) | 2200 | 1800 | 2400 | 2000 | — |
| Protein adsorption amount (μg/cm$^2$) | 0.16 | 0.32 | 0.15 | 0.14 | 1.89 |
| Protein adsorption amount after durability testing (μg/cm$^2$) | 0.17 | 0.34 | 0.155 | 0.145 | 2.25 |
| Rate of increase | 6% | 6% | 3.3% | 3.5% | 19% |

The results of Table 1 show that the surface-modified bodies of the examples each had a low protein adsorption amount, and also exhibited a low rate of increase in protein adsorption amount after repeated adsorption and washing. In contrast, the untreated PET surface in Comparative Example 1 even initially had a large adsorption amount, and also exhibited a high rate of increase in protein adsorption amount after repeated adsorption and washing. It should be noted that since cells adhere or adsorb to the surface via proteins adsorbed thereon, a lower protein adsorption amount indicates that cells are also less likely to adhere or adsorb.

These results demonstrated that by forming polymer chains on the surface of a matrix, filter, channel or tube for medical and healthcare use, or the like using a hydrophilic monomer such as acrylamide or 2-methacryloyloxyethyl phosphorylcholine, it is possible to reduce protein adsorption and cell adsorption and at the same time to provide durability after repeated use.

Moreover, the results of Examples 7, 9, and 10 demonstrated that when the PET surface is irradiated with UV light having a wavelength of 300 nm or less prior to the step 1, or when alcohol washing or autoclave treatment is performed after the step 2, protein adsorption and cell adsorption can be further reduced, and durability after repeated use can also be further improved.

Furthermore, the 2-methoxyethyl acrylate polymer grown in Example 7 is a material that does not adsorb platelets, white blood cells, and red blood cells in blood, but selectively adsorbs only cancer cells. This polymer can be expected to be used for selective adhesion or adsorption of only cancer cells in blood containing cancer cells.

The invention claimed is:

1. A method for surface-modifying an object made of a thermoplastic resin, wherein the object is a matrix, filter, channel, or tube configured for medical or healthcare use and for contact with blood or biological fluids and wherein the thermoplastic resin is polyethylene terephthalate or polystyrene, the method comprising:

a step 1 of forming polymerization initiation points on a surface of the object, wherein said step 1 comprises adsorbing a photopolymerization initiator to the surface of the object to form the polymerization initiation points from the photopolymerization initiator on the surface; and a step 2 of radically polymerizing an alkoxyalkyl (meth) acrylate hydrophilic monomer starting from the polymerization initiation points by irradiation with UV light having a wavelength of 300 to 400 nm to grow polymer chains on the surface of the object, wherein the photopolymerization initiator is a benzophenone compound;

wherein the hydrophilic monomer is a 2-methoxyethyl acrylate monomer;

wherein during or before the irradiation, an inert gas is inserted into a reaction vessel, a reaction tube, and a reaction solution, and the hydrophilic monomer is polymerized in an atmosphere replaced with the inert gas;

wherein the radical polymerization of the hydrophilic monomer in the step 2 is carried out by applying or spraying a solution of the hydrophilic monomer onto the surface of the object, and then covering the applied or sprayed object with a transparent cover of glass or resin, followed by the irradiation with the UV light through the transparent cover of glass or resin to radically polymerize the hydrophilic monomer;

wherein the surface of the surface-modified object has reduced protein adsorption ranging from 0.13-0.34 µg/cm$^2$ of bovine serum albumin as compared to the unmodified surface of the object;

wherein the polymer chains each have a length of 800 to 3000 nm.

2. The method according to claim 1, wherein the surface of the object is irradiated with UV light having a wavelength of 300 nm or less prior to the step 1.

3. The method according to claim 1, wherein after the step 2, the surface-modified object on which the polymer chains are grown is washed.

4. The method according to claim 3, wherein the washing is carried out by at least one selected from the group consisting of hot water washing, alcohol washing, and acetone washing.

5. The method according to claim 1, wherein a solution of the hydrophilic monomer contains a polymerization inhibitor, and the hydrophilic monomer is polymerized in the presence of the polymerization inhibitor.

6. The method according to claim 5, wherein the polymerization inhibitor is 4-methylphenol.

* * * * *